United States Patent
Haunschild et al.

(10) Patent No.: US 8,216,265 B2
(45) Date of Patent: Jul. 10, 2012

(54) MEDICAL INSTRUMENT FOR PUNCHING OUT TISSUE

(75) Inventors: Karl-Heinz Haunschild, Muehlheim (DE); Jochen Schmidberger, Schoerzingen (DE)

(73) Assignee: Karl Storz GmbH & Co. KG (DE)

( * ) Notice: Subject to any disclaimer, the term of this patent is extended or adjusted under 35 U.S.C. 154(b) by 562 days.

(21) Appl. No.: 12/234,042

(22) Filed: Sep. 19, 2008

(65) Prior Publication Data

US 2009/0082799 A1    Mar. 26, 2009

(30) Foreign Application Priority Data

Sep. 21, 2007   (DE) .................. 10 2007 046 397

(51) Int. Cl.
*A61B 17/32* (2006.01)
(52) U.S. Cl. ........................................ 606/184
(58) Field of Classification Search ............ 606/167, 606/170, 184–188; 600/562–564, 566, 567
See application file for complete search history.

(56) References Cited

U.S. PATENT DOCUMENTS

| | | | | |
|---|---|---|---|---|
| 1,167,014 A | * | 1/1916 | O'Brien | 606/151 |
| 2,505,358 A | * | 4/1950 | Gusberg et al. | 600/564 |
| 3,837,345 A | * | 9/1974 | Matar | 606/159 |
| 5,300,023 A | * | 4/1994 | Lowery et al. | 604/515 |
| 5,573,008 A | * | 11/1996 | Robinson et al. | 600/567 |
| 5,628,762 A | | 5/1997 | Al-Tameem | |
| 5,893,369 A | * | 4/1999 | LeMole | 606/184 |
| 5,910,153 A | * | 6/1999 | Mayenberger | 606/184 |
| 6,673,088 B1 | * | 1/2004 | Vargas et al. | 606/185 |
| 6,689,147 B1 | * | 2/2004 | Koster, Jr. | 606/184 |
| 6,695,859 B1 | * | 2/2004 | Golden et al. | 606/184 |
| 6,863,677 B2 | * | 3/2005 | Breznock | 606/184 |
| 2003/0069595 A1 | | 4/2003 | Phung et al. | |
| 2006/0052808 A1 | * | 3/2006 | Stammberger | 606/170 |

FOREIGN PATENT DOCUMENTS

| | | |
|---|---|---|
| DE | 10342002 A1 | 4/2005 |
| EP | 1750600 B1 | 1/2008 |
| GB | 2044103 A | 10/1980 |
| WO | 2007098354 A1 | 8/2007 |

OTHER PUBLICATIONS

European Search Report; EP 08 16 4508; Aug. 13, 2009; 4 pages.

\* cited by examiner

*Primary Examiner* — Elizabeth Houston
(74) *Attorney, Agent, or Firm* — St. Onge Steward Johnston & Reens LLC

(57) ABSTRACT

Medical instrument serves to punch out tissue. It has a shaft, a first cap-shaped tool arranged at a distal end of said shaft and having a circular cutting edge. A second tool has a circular cutting edge at a distal end thereof. Said first and said second tool can be shifted relative to one another along said shaft thereby that second tool can enter into the cavity of that first tool. Said second tool bears a plate-like element, distally spaced apart from its cutting edge, said plate-like element has an extension in a cross-section plane corresponding to a clear internal cross-section plane of said cavity.

9 Claims, 3 Drawing Sheets

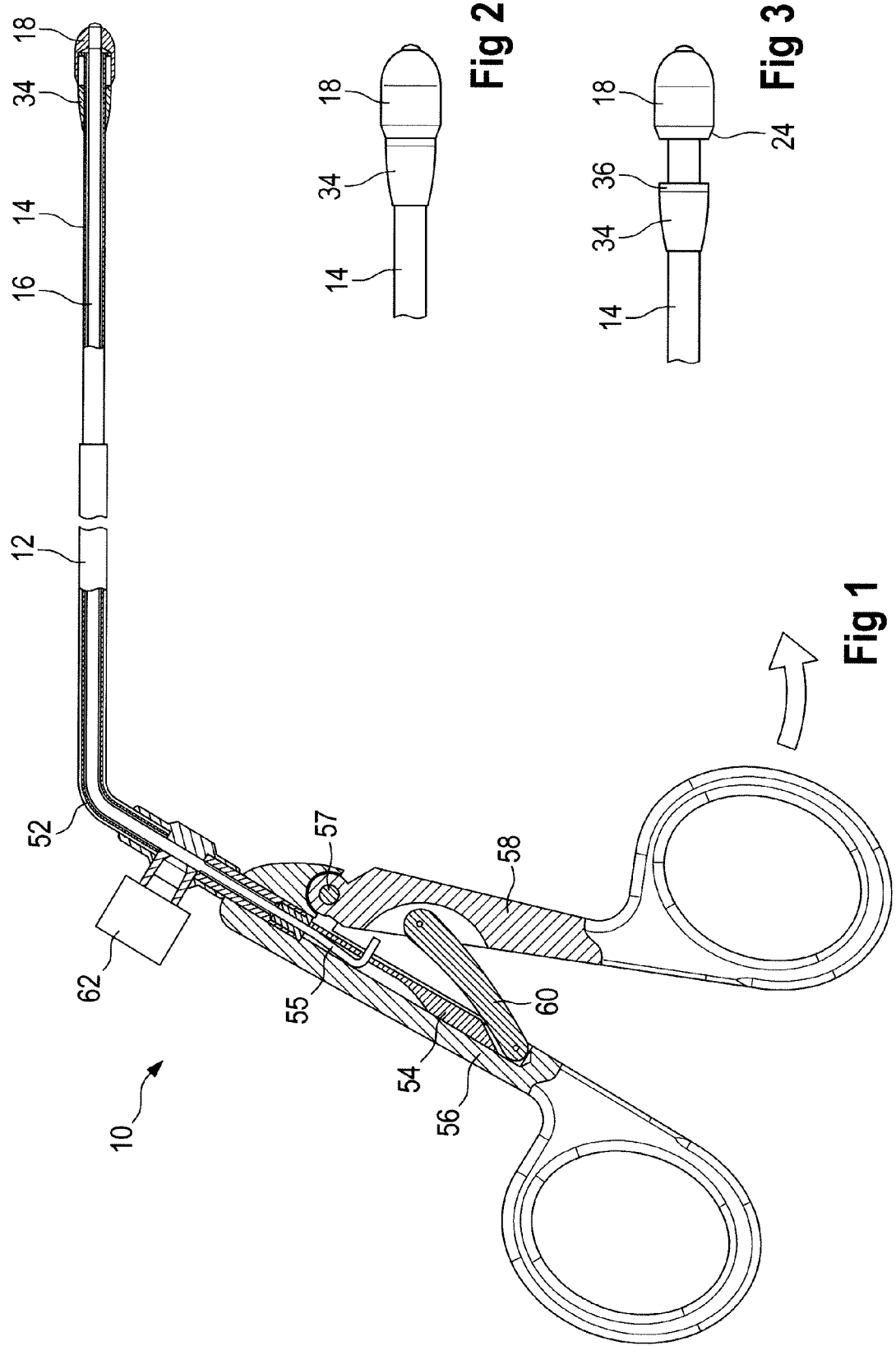

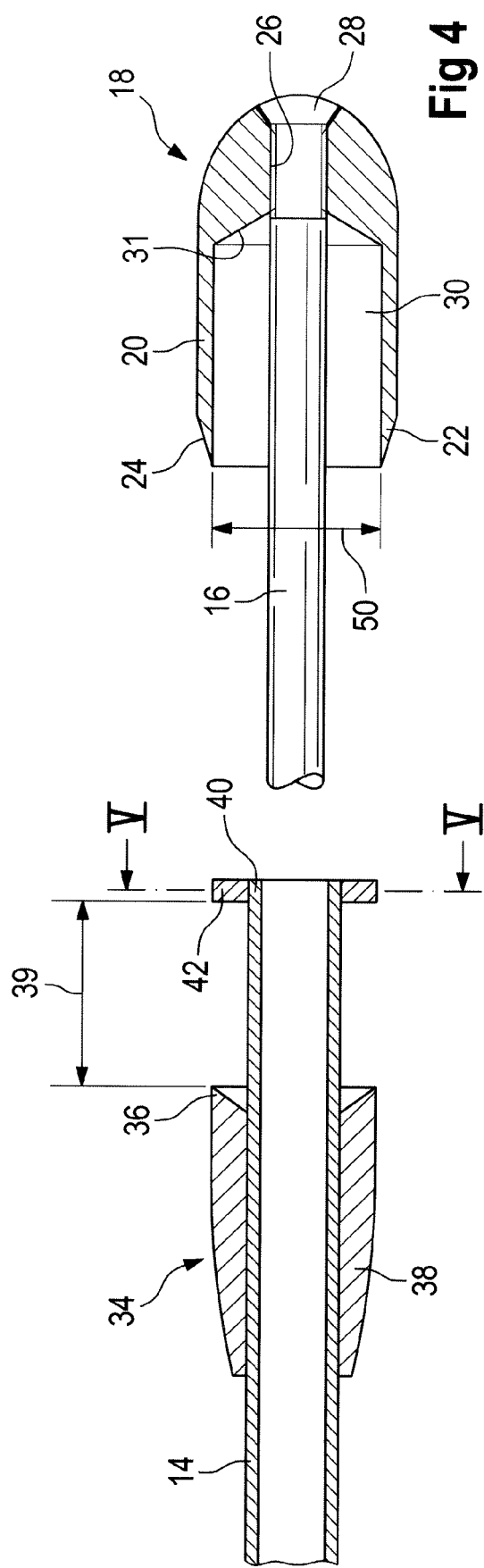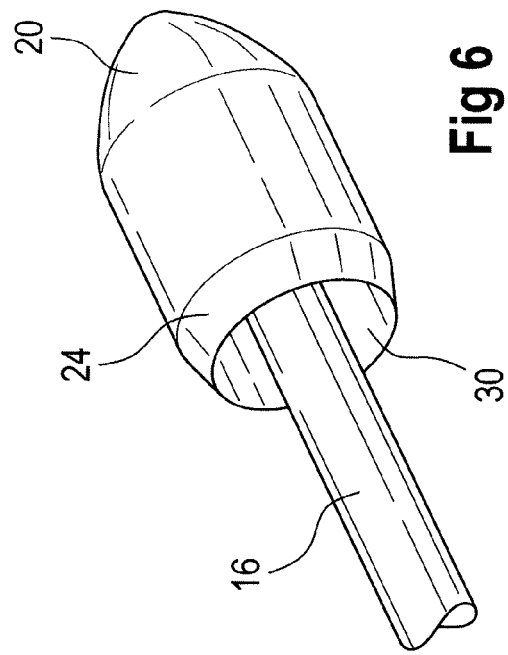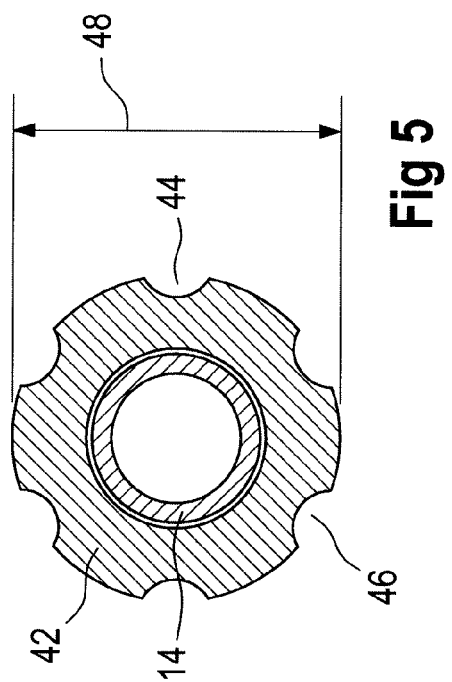

MEDICAL INSTRUMENT FOR PUNCHING OUT TISSUE

BACKGROUND OF THE INVENTION

The invention relates to a medical instrument for punching out tissue.

A medical instrument of this kind is known from DE-A-103 42 002. The known medical instrument has a first cap-shaped tool arranged at a distal end of a shaft, which proximally has a circular cutting edge, with a second tool, which distally has a circular cutting edge, whereby both tools can be shifted relative to one another along the shaft, whereby the cutting edge of the second tool can be introduced into an inner cavity of the first cap-shaped tool and both cutting edges cooperate in the manner of a punch.

These medical instruments are also described as egghead or mushroom head punches.

Such medical instruments are widely used in endoscopic diagnosis, surgery and aftercare for paranasal sinuses and the front base of the skull. Their purpose for example is to open the ethmoid bone cells or the sphenoid bone cavity.

The first tool arranged at the distal end of a shaft is designed as a cap, e.g. a mushroom or an egg, so that it can be introduced into or through small body openings either naturally occurring or artificially made.

The second tool has a cutting edge which is facing the cutting edge of the first tool. The second tool is designed such that it can enter the inner cavity of the first tool at least with its cutting edge. In the process the extensive cutting edges slide closely past one another, separating any tissue in between. Both cutting edges work in the manner of a punch through their circular cutting edges. To operate the tools one is mostly fixed and the other is mobile so that both tools can be moved between an open position, in which both cutting edges are at a distance from one another, and a closed state, in which the cutting edge of the second tool is introduced into the cutting edge of the first tool.

The planes made by the circular cutting edges can run perpendicularly to the longitudinal axis of the shaft, but they can also run at an angle thereto.

The shaft itself can be straight or curved so as to be able to access sinuses in particular when employed in the ENT (ear, nose and throat) region.

During the punching or cutting edge procedure the second tool, which enters the inner cavity of the first tool, pushes or respectively pulls the separated tissue into this cavity.

Because the tools are relatively small (standard diameter variables of such a punch head are in the range of 0.1 to 0.2 inch), it is very difficult to remove the separated tissue from the inner cavity once the tools are open.

It is therefore object of the present invention to provide measures making it easier to remove tissue from the inner cavity of the first tool, i.e. from the egghead or mushroom head.

SUMMARY OF THE INVENTION

This object is achieved by a medical instrument for punching out tissue comprising a shaft, a first cap-shaped tool arranged at a distal end of said shaft, said first cap-shaped tool having a circular cutting edge at a proximal end of said tool and an inner cavity housing said shaft, a second tool having a circular cutting edge at a distal end thereof, said first cap-shaped tool and said second tool can be shifted relative to one another along said shaft, said circular cutting edge of said second tool thereby can enter said inner cavity of said first cap-shaped tool, said cutting edges of said tools cooperate in a manner of a punch when said circular cutting edge of said second tool enters said inner cavity of said first cap-shaped tool, wherein said second tool bears a plate-like element distally spaced apart from its cutting edge, said plate-like element has an extension in a cross-section plane corresponding to a clear internal cross-section plane of said cavity around said shaft.

One advantage is that the plate-like element protruding distally over the second tool in front of the cutting edge, and well before any separation or punching procedure has taken place, runs into the inner cavity of the first tool. The plate-like element quasi forms a movable end wall of the inner cavity of the first tool.

During the actual cutting or respectively punching procedure tissue is moved into the inner cavity via the cutting edge of the second tool. At the same time the plate-like element enters the cavity, but ahead of the tissue. This continues until the plate-like element is at a distal end of the cavity. This corresponds to a closed position of the tools.

When the tools are opened the tissue previously moved into the inner cavity of the first tool is now moved out of the inner cavity of the first cap-like tool by the plate-like element of the second tool.

The plate-like element thus acts as a type of rake blade or respectively as a stripper/retention plate. In other words, all the tissue separated by the separation procedure and pushed into the inner cavity of the first tool is cleared out of this cavity via the plate-like element when the second tool is withdrawn from the first tool.

The advantage is that the tissue taken up in the inner cavity is inevitably removed when the tools are opened.

Because the plate-like element must enter a base-side closed cavity it does not precisely cover the entire clear internal cross-section, rather there is sufficient space left for the air present inside the cavity to be able to escape. Nevertheless it is ensured that all the tissue is cleared out of the inner cavity when the opposite movement is made.

In a further embodiment of the invention when the tools are in an open position the plate-like element of the second tool comes to rest at the level of the proximal-side cutting edge of the first tool.

The advantage to this step is that when the tools are in the open state the plate-like element of the second tool constitutes a proximal-side seal, therefore virtually a cover of the inner cavity of the first tool.

This prevents contaminants from being able to penetrate the inner cavity for example prior to the actual punching procedure.

In a further embodiment of the invention when the tools are in a closed position the plate-like element of the second tool comes to rest at the level of a distal end of the cavity.

The advantage to this step is that approximately the entire inner space of the cavity can be used for receiving the punched out tissue.

Otherwise expressed, the plate-like element can be moved over the entire axial length of the cavity, and can consequently strip the latter over its full length.

In a further embodiment of the invention the plate-like element has at least one recess.

The advantage to this step is that via this recess pressure equalisation is specifically possible with moving the plate-like element into the cavity or respectively moving it out.

In a further embodiment of the invention the at least one recess is designed as a longitudinal notch on the periphery.

The advantage to this step is that a large-area rake blade is available which has only one or more longitudinal notches to enable air balance.

In a further embodiment of the invention the first cap-shaped tool is connected to a rod-like actuation element.

The advantage to this step is that via the rod-like actuation element the first cap-shaped tool can be designed as the mobile tool and can be moved in both directions.

In a further embodiment of the invention the second tool is arranged on a tube element of the shaft.

The advantage to this step is that the second tool can be designed as an immobile tool which can absorb and distribute the forces via the shaft during the actual separation procedure. In the ENT area relatively hard pieces of cartilage and bone are removed, requiring considerable forces.

In a further embodiment of the invention the rod-like actuation element, which is connected to the first tool, is guided in the tube element bearing the second tool.

The advantage to this step is to enable a highly stable and compact construction, and that during the relative movements both tools can be guided precisely, for example by the outer diameter of the rod-like actuation element approximately corresponding to the clear inner diameter of the tube element.

In the event also of the effect of high forces it can be excluded that the circular cutting edges are radially offset, which would negatively influence the punching result.

If the aim is for the first tool to be stationary and the second tool to be moved, the tube element can be shifted and the rod-like actuation element is stationary.

In a further embodiment of the invention the plate-like element is attached at the distal end of the tube element.

The advantage to this step is that the inventive plate-like element can be provided structurally very easily, for example by a correspondingly formed annular disc being welded onto the distal end of the tube element.

It is understood that the abovementioned characteristics and those yet to be explained hereinbelow can be used not only in the respectively specified combination, but also in other combinations or on their own, without departing from the scope of the present invention.

BRIEF DESCRIPTION OF THE DRAWINGS

Embodiments of the invention are illustrated in the diagrams and will now be explained in greater detail in the following description, in which:

FIG. 1 shows a side elevation of an inventive instrument in partial section;

FIG. 2 shows a slightly enlarged side elevation of the distal end of the instrument of FIG. 1 with closed tools;

FIG. 3 is a view comparable to the view of FIG. 2 with opened tools;

FIG. 4 shows a lengthways section of both tools in an exploded view;

FIG. 5 shows a section along the line V-V in FIG. 4 on an enlarged scale;

FIG. 6 shows a perspective view of the first tool substantially from proximally to distally;

DETAILED DESCRIPTION OF A PREFERRED EMBODIMENT

Figure 7:
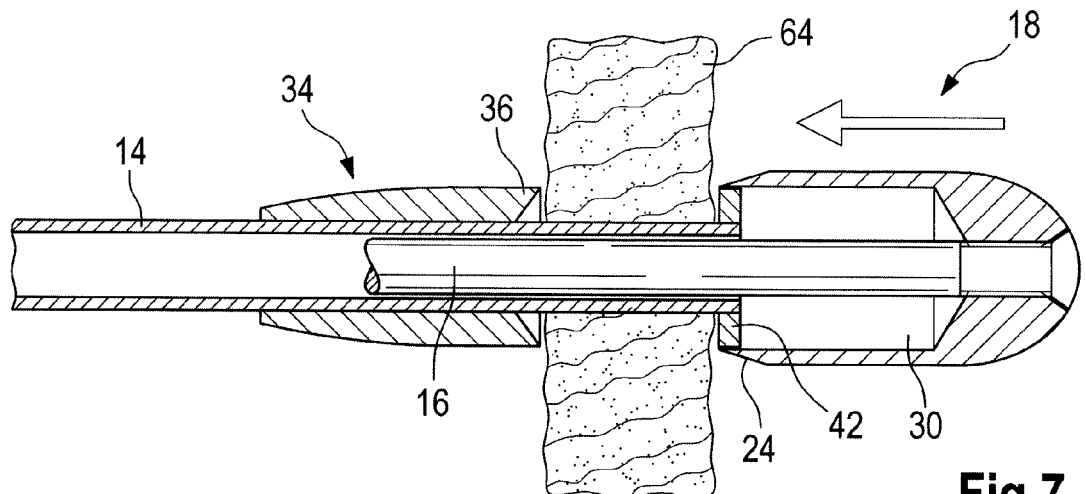
FIG. 7 shows a side section in the region of the distal end of the instrument of FIG. 1 with opened tools prior to performing a punching procedure on tissue.

An inventive instrument illustrated in FIG. 1 is designated in its entirety by reference numeral 10.

The instrument 10 has an elongated shaft 12 which has a tube element 14 on the distal side.

A rod-like actuation element 16 is housed inside the tube element 14 or respectively the hollow shaft 12.

As is evident in particular from the illustration of FIG. 4 the rod-like actuation element 16 bears a first tool 18 on the distal side.

The first tool 18 has a body in the form of a cap 20 which can be shaped like the head of an egg or of a mushroom. The cap 20 is provided with a circular cutting edge 24 at its proximal end 22.

In the region of its vertex the cap 20 has an opening 26, into which the rod-like actuation element 16 is inserted, or is attached there by a screw 28. This connection can also be made by welding.

A cavity 30, with a closed distal end 31, thus exists in the interior of the cap 20 The cavity 30 is open on the proximal side.

As also is evident from FIG. 4, the tube element 14 of the shaft 12 bears a second tool 34. The second tool 34 bears a circular cutting edge 36 on the distal side.

The second tool 34 is designed as a sleeve 38 which is slipped onto the tube element 14 and is welded thereto.

As is evident in particular from FIG. 4, the tube element 14 on the distal side projects out over the second tool 34 and by the distance 39.

A plate-like element 42 is attached to the distal end 40, for example by laser welding, which assumes the form of an annular plate, as is evident in particular from the enlarged sectional illustration of FIG. 5. The outer diameter 48 of the plate-like element 42 corresponds approximately to the clear inner diameter 50 of the cavity 30 in the first tool 18.

The distance 39, i.e. the distance between cutting edge 36 of the second tool 34 and the plate-like element 42, corresponds approximately to the depth of the cavity 30.

As is evident in particular from FIG. 5, various recesses 44 are provided circumferentially on the plate-like element 42, which in the illustrated embodiment are configured in the form of longitudinal notches 46 with a circular-section cross-section.

The outer diameter of the rod-like element 16 corresponds to the clear inner diameter of the tube element 14.

If the aim is to be able to convey flushing fluids via the tube element 14 to the tools 18, 34, the cross-section of the rod-like element 16 is not round, rather for example triangular or longitudinally notched, enabling transport of either liquid or gas.

It is evident from the exploded view of FIG. 4 that in this position the rod-like actuation element 16 can be pushed into the tube element 14.

If the plate-like element 42 has reached the cutting edge 24 of the first tool 18, whereby, as will be explained hereinbelow, this corresponds to the open position of the tools 18, the plate-like element 42 constitutes a proximal-side seal of the cavity 30. If the second tool 36 is advanced further the plate-like element 42 enters into the cavity 30 to reach its distal end 31. This corresponds to the closed position of the rods.

It is also evident from FIGS. 4 to 6 that the approximately annular plate-like element 42 approximately covers the clear internal cross-section 50 of the cavity 30. The cross-section is taken perpendicular to a longitudinal axis of the shaft 12.

With reference again to FIG. 1, it is apparent that the rod-like actuation element 16 is guided to a sled 54 via a curve 52, where its angled end 55 is suspended in the sled 54.

The rod-like actuation element 16 is thus designed as ductile wire.

The sled 54 can be held displaceably in the longitudinal direction of the rod-like actuation element 16 in a first grip part 56 which represents the immobile grip part. A second grip part 58 is articulated to the first grip part 56 via a trunnion 57.

A shackle 60, which is articulated to the second mobile grip part 58 on the one hand and to the sled 54 in the first grip part 56 on the other hand, extends between both grip parts 56 and 58.

If the mobile grip part 58 moves into the position illustrated in FIG. 1 the first tool 18 is drawn in to the maximum, and in such a way that the cutting edge 36 of the second tool 34 has passed by the cutting edge 24 of the first tool. This state is illustrated in FIG. 1 or FIG. 2 and corresponds to the closed position of both tools 18, 34.

If the mobile grip part 58 is now moved in the direction of the arrow illustrated in FIG. 1 the rod-like actuation element 16 is displaced distally. The first tool 18 connected to the latter is thus moved away from the second tool 34, as shown in FIG. 3. This position corresponds to the open position of the tools 18 and 34.

If the aim is for the first tool 18 to be fixed and the second tool 34 to be moved, the sled 54 is connected via a push wire piece to the tube element 14 now designed to be shiftable. The actuation element 14 is then attached immovably to the shaft 12.

FIG. 1 shows that a stud 62 protrudes to the side, via which flushing fluids can be introduced to the inside of the hollow shaft 12 or respectively of the tubular element 14. It must accordingly be ensured that these fluids can reach as far as distally, either through corresponding longitudinal notches on the outside of the actuation element 16 or via the previously described configuration having for example a triangular cross-section.

Functioning of the medical instrument 10 will now be described in greater detail by means of the image sequence in FIGS. 7 to 9. In FIG. 7 both tools 18 and 34 are shown in the open position, therefore as described for example in FIG. 3.

It is evident there that the plate-like element 42 forms a proximal-side end to the inner cavity 30 of the first tool 18, therefore coming to rest approximately at the height of its circular cutting edge 24.

The cutting edge 36 of the second tool 34 lies at a distance from the cutting edge 24 of the first tool 18, therefore at the distance 39 described in FIG. 4. Tissue 64 to be punched out is now present between both cutting edges 24 and 36.

The cutting edges 24 and 36 of both tools 18 and 34 can be put either to the side on the tissue 64, or, if a small opening present in the tissue 64 is to be enlarged, the cap-shaped first tool 18 can first be pushed in through such an opening. If the actuation element 16 is moved proximally, as indicated in FIG. 7 by an arrow (or the tool 34 is moved in the opposite direction), the cutting edge 24 moves to the cutting edge 36 and accordingly separates off a section of tissue 66 which is then trapped in the inner cavity 30, as evident from FIG. 8.

Figure 8:
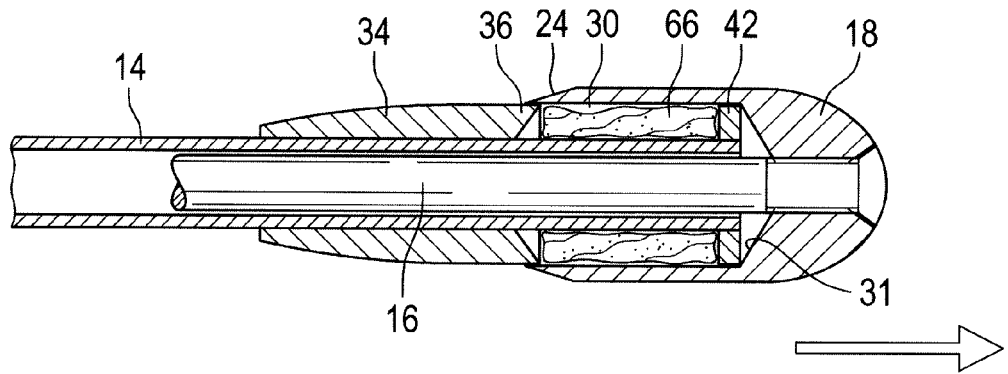
FIG. 8 shows a section comparable to FIG. 7 with closed tools with punched-out tissue.

As also is evident from FIG. 8, the plate-like element 42 has in the process moved as far as the distal end 31 of the cavity 30 and thus forms a distal seal of the cavity 30.

Figure 9:
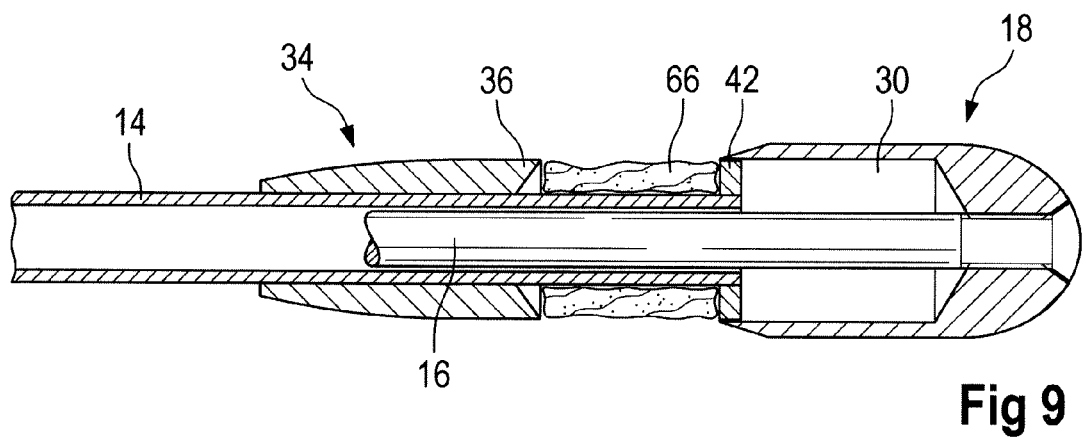
FIG. 9 is a view comparable to the view of FIG. 7 after the tools have been reopened and with separated tissue cleared out of the first tool.

If the tools 18 and 34 are now reopened, as is evident from the transition of FIG. 8 to FIG. 9, the plate-like element 42 pushes the section of tissue 66 caught up in the cavity 30 out of the latter. The plate-like element 42 thus functions in the manner of a rake blade or stripper plate. In the position in FIG. 9 the separated section of tissue 66 can be removed without difficulty from here on. It is also evident that the cavity 30 is completely empty, i.e. not covered by tissue parts or contaminated. After the section of tissue 66 is removed the instrument 10 is immediately ready for use for a subsequent punching procedure.

The circumferential notches 46 in the plate-like element 42 (see FIG. 5) ensure that movement can take place with air balance, i.e. the air present in the cavity 30 can exit via the notches 46 from the cavity 30 or respectively then re-enter.

The cutting edges 24 and 36 explained in the above-described embodiments in each case run in a plane aligned perpendicularly to the longitudinal axis of the shaft 12 or respectively of the tube element 14.

The configuration of the invention with the plate-like element 42 can also be employed for cutting edges 36 or respectively 24 which run at an incline to this longitudinal axis, as is the case for example in DE-A-103 42 002, mentioned at the outset.

Then the plate-like element 42 can, as in the illustrated embodiment, likewise extend in a plane aligned perpendicularly to the longitudinal axis of the tube element 14, or the plate-like element 42 can accordingly be inclined just as the cutting edges are.

What is claimed is:

1. A medical instrument for punching out tissue comprising:
    a shaft,
    a first cap-shaped tool arranged at a distal end of said shaft, said first cap-shaped tool having a circular cutting edge at a proximal end of said tool and an inner cavity housing said shaft,
    a second tool having a circular cutting edge at a distal end of said second tool, said first cap-shaped tool and said second tool can be shifted relative to one another along said shaft, said circular cutting edge of said second tool can enter said inner cavity of said first cap-shaped tool, said cutting edges of said tools cooperate in a manner of a punch when said circular cutting edge of said second tool enters said inner cavity of said first cap-shaped tool, and
    a plate-like element fixedly attached to said second tool and being distally spaced apart from said cutting edge of said second tool at a fixed distance, said plate-like element has an extension in a cross-section plane corresponding to a clear internal cross-section plane of said cavity around said shaft.

2. The medical instrument of claim 1, wherein said tools can be moved between an open position and a closed position, wherein in said open position, said plate-like element of said second tool being positioned at said proximal-side cutting edge of said first tool.

3. The medical instrument of claim 1, wherein said tools can be moved between an open position and a closed position, wherein in said closed position, said plate-like element of said second tool being positioned at a distal end of said cavity.

4. The medical instrument of claim 1, wherein said plate-like element has at least one recess.

5. The medical instrument of claim 4, wherein said at least one recess is designed as a longitudinal notch on a periphery of said plate-like element.

6. The medical instrument of claim 1, wherein said first cap-shaped tool is connected to a rod-like actuation element.

7. The medical instrument of claim 6, wherein said second tool is arranged on a tube element of said shaft.

8. The medical instrument of claim 7, wherein said rod-like actuation element is introduced into said tube element.

9. The medical instrument of claim 8, wherein said plate-like element is attached to a distal end of said tube element.

\* \* \* \* \*